United States Patent
Mueller

(10) Patent No.: US 8,571,811 B1
(45) Date of Patent: Oct. 29, 2013

(54) DOUBLE-SIDED RAPID DRIFT CORRECTION

(75) Inventor: Michael Mueller, Portland, OR (US)

(73) Assignee: Digital Control Systems, Inc., Portland, OR (US)

( * ) Notice: Subject to any disclaimer, the term of this patent is extended or adjusted under 35 U.S.C. 154(b) by 661 days.

(21) Appl. No.: 12/657,617

(22) Filed: Jan. 22, 2010

(51) Int. Cl.
*G01N 31/00* (2006.01)

(52) U.S. Cl.
USPC .......................................................... 702/23

(58) Field of Classification Search
USPC .......................................................... 702/23
See application file for complete search history.

(56) References Cited

U.S. PATENT DOCUMENTS

| 5,347,474 A | 9/1994 | Wong |
| 6,526,801 B2 | 3/2003 | Kouznetsov |

*Primary Examiner* — Stephen Cherry
(74) *Attorney, Agent, or Firm* — James E. Harris

(57) ABSTRACT

A method and system for gas sensor drift correction is disclosed, appropriate for use in a system placed in an environment that with some regularity reaches a background gas concentration. A background gas concentration range is defined. When the gas sensor readings drop below the background gas concentration range for at least a defined short dwell time, an upwards calibration adjustment is effected. When the gas sensor readings stay above the background gas concentration range for a defined long dwell time (longer than the maximum expected interval between excursions to the background gas concentration), a downwards calibration adjustment is effected.

20 Claims, 8 Drawing Sheets

DOUBLE-SIDED RAPID DRIFT CORRECTION

BACKGROUND

1. Field of the Invention

The present disclosure relates generally to environmental gas sensors, and more particularly to sensor drift correction for such sensors.

2. Description of Related Art

Environmental gas sensors generally detect the presence of a constituent gas in a gas mixture. For instance, one common application of environmental gas sensing is the measurement of carbon dioxide ($CO_2$) concentration in an ambient environment such as an office, meeting room, greenhouse, or exhaust stream.

Non-Dispersive Infrared (NDIR) gas sensors represent a large segment of the existing $CO_2$ sensor market. FIG. 1 contains a block diagram for a typical NDIR sensor 100. A gas sensor 110 contains a measurement chamber, into which an ambient gas mixture is either forced or diffused. Radiation of a wavelength absorbed by $CO_2$ is introduced into the chamber by a radiation source, and a radiation sensor measures the amount of unabsorbed radiation. Generally gas sensor 110 also contains an analog amplifier, and outputs an amplified electrical signal representative of the radiation sensor reading. An analog to digital (A/D) converter 120 periodically digitizes the analog signal and supplies the digitized readings to a processor 130. Processor 130 uses programming instructions and calibration values stored in memory 140 to convert the readings to desired outputs. The outputs may be displayed or encoded $CO_2$ readings in parts per million (PPM) units, voltage- or current-coded control signals to control air handling equipment, etc.

In one typical application, a $CO_2$ sensor is deployed in a building to assist the air handling system in controlling the amount of fresh air supplied to various areas of the building. When a measured room or area is unoccupied, the $CO_2$ readings decrease toward a background level, even with minimal fresh air introduction. During the times that the building is occupied, however, $CO_2$ readings can rapidly increase from the background level. For an office building that is occupied during the day but not at night, FIG. 2 shows an exemplary plot 200 of measured $CO_2$ concentration versus time. The line marked "SETPOINT" is the desired maximum $CO_2$ concentration. During the time of day that the building is occupied, the $CO_2$ concentration rises to SETPOINT and is then controlled around that point. As the building becomes vacant or near-vacant at the end of the workday, the $CO_2$ concentration decreases toward the background level, until the next time period in which the building becomes occupied.

Almost all NDIR sensors exhibit sensor drift over time, due to contaminants on and/or corrosion of the measurement chamber, aging of the light source, sensors, filters, and amplifiers, etc. Although recalibration using known sample gas mixtures is possible, it is often inconvenient to recalibrate sensors often enough to avoid significant drifts.

Without recalibration, drifting sensor readings cause a controlled system to control to a different maximum concentration, and uncontrolled systems to report in error. FIG. 2 contains a plot 200 of measured concentration versus time. Plot 200 shows sensor drift producing measured values that, over time, decrease below the actual $CO_2$ readings. FIG. 3 contains a similar time history of measured values that, over time, increase above the actual $CO_2$ readings. In the FIG. 2 scenario, the result is that the control setpoint gradually allows for a greater $CO_2$ concentration than that desired during the building-occupied portions of the day. In the FIG. 3 scenario, the result is that the control setpoint gradually allows for a lower $CO_2$ concentration that that desired during the building-occupied portions of the day.

For a $CO_2$ sensor used in an application where the measured ambient frequently falls to a background $CO_2$ concentration, algorithms have been developed to compensate for sensor drift. U.S. Pat. No. 6,526,801 contains an example of a prior art sensor drift correction algorithm. The algorithm attempts to discern "quiescent periods" during which the $CO_2$ concentration remains stable. When such a quiescent period is found, an estimated $CO_2$ concentration and time observed for that period is added to a list of other quiescent periods that have been observed. When a quiescent period seems to grossly disagree with other observed readings, it may be rejected. After many such readings have been logged, a curve fit that estimates sensor drift is applied to the readings. FIGS. 2 and 3 show example curve fits, assuming that "quiescent periods" have been found that correspond to baseline $CO_2$ levels.

Once a curve fit has been estimated, the difference between a set baseline $CO_2$ level and the value of the curve as projected to the current time is used to adjust the sensor readings going forward in time. This allows gradual, predictable sensor drifts to be compensated in order to add a measure of long-term stability to the sensor output.

BRIEF DESCRIPTION OF THE DRAWINGS

The present invention can be best understood by reading the specification with reference to the following Figures, in which.

DETAILED DESCRIPTION

The present disclosure presents alternatives to prior art drift compensation algorithms. In at least some configurations, the drift compensation embodiments described herein can achieve advantages over prior art approaches. One achievable advantage is simplicity—described embodiments can greatly reduce or even eliminate many of the history-keeping, judgment, and calculation functions required by prior art drift compensation approaches, thus potentially lowering cost and lowering the impact of an event such as a loss of power (and therefore data) that could impact an algorithm that works from a historical database, or erroneous drift compensation due to inaccurate judgments. Another advantage of the embodiments is correction speed—particularly for drifts that underestimate the $CO_2$ concentration, described drift compensation embodiments can swiftly and accurately combat such drifts. It is recognized herein that the limitations that require a more cautions approach to combating upward measurement drift really do not exist for downward drift, thus allowing an asymmetric approach to correction. Where drifts fail to follow a smooth time curve, the described algorithms can still respond accurately without the errors and time lag involved in a curve-fitting predictive approach.

Briefly, the embodiments described herein acknowledge that for unattended NDIR sensors, absolute accuracy down to a few PPM is unrealistic. The drift correction algorithms described herein instead establish a background concentration range for minimum concentration. Assuming that, absent error, the measured ambient will never fall below this range, any readings below this range can be swiftly corrected back up toward the range using a calibration adjustment. When measured concentration fails to ever drop into the minimum concentration range, on the other hand, a drift constant can be adjusted to nudge minimum concentration back towards the range. These methods need not establish a drift rate or curve, and require minimal or no historical readings in order to operate.

Figure 5:
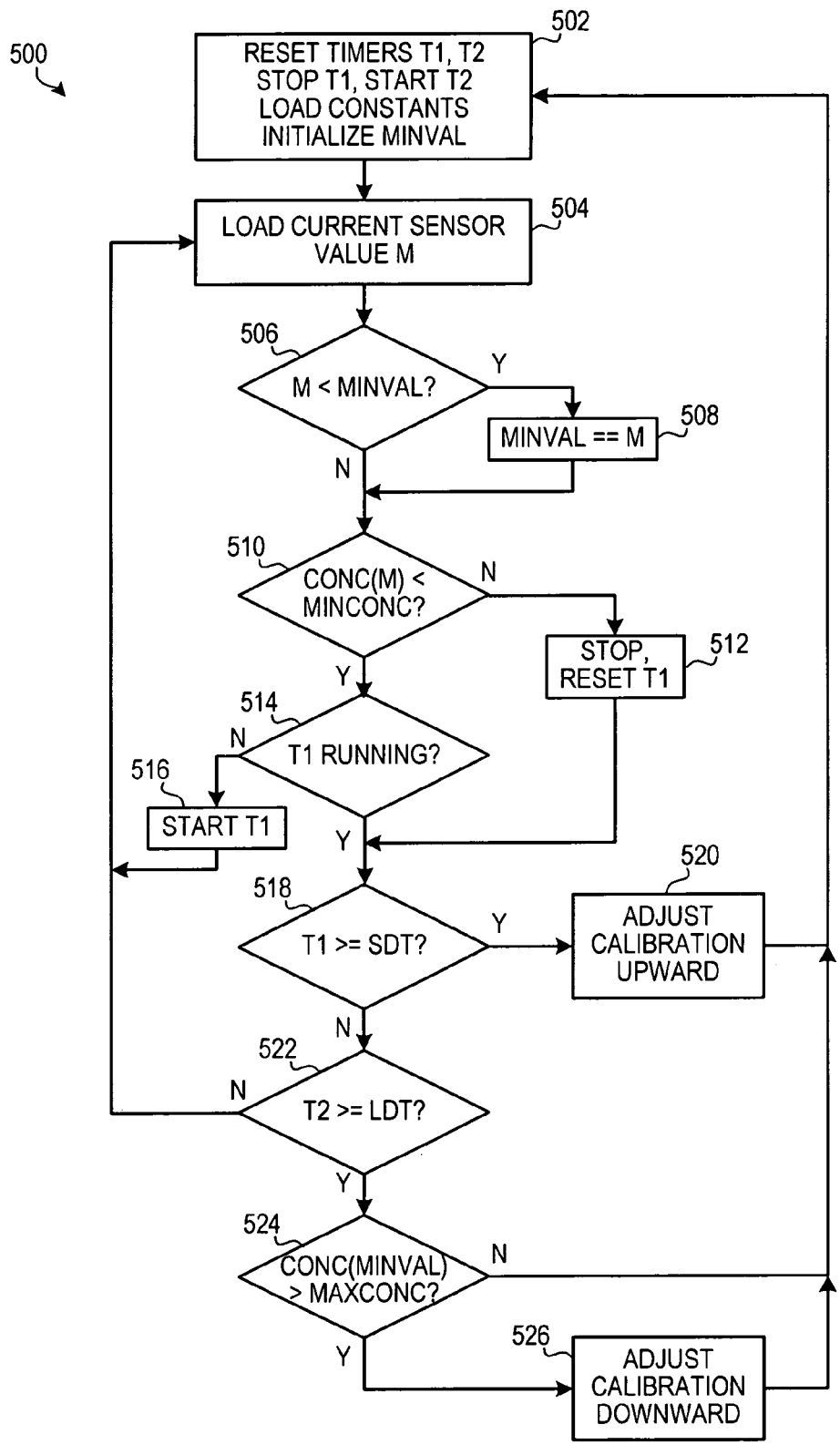
FIGS. 5 and 6 contains flowcharts for baseline drift correction algorithms according to several embodiments.

FIG. 5 contains a flowchart 500 for a drift correction method according to an embodiment. The method employs several constants:

Maximum Concentration (MAXCONC): an upper bound for a defined background concentration level range Minimum Concentration (MINCONC): a lower bound for the defined background concentration level range Short Dwell Time (SDT): a minimum contiguous time interval that the sensor must produce readings below MINCONC in order to trigger an upwards calibration adjustment Long Dwell Time (LDT): a minimum contiguous time interval during which the sensor should produce at least some readings below MAXCONC, or otherwise trigger a downwards calibration adjustment Calibration Adjustment Value (CalAdj): the calibration adjustment step size.

The FIG. 5 method runs on a processor, with attached memory, having access to sensor readings to which drift compensation will be applied. The method and constants will typically be coded into firmware stored in non-volatile memory and accessible to the processor. The various constants can be either hardcoded or adjustable, e.g., settable through a front panel menu, remote web interface, etc. Upon a power-on or reset event, the processor begins execution of executable code represented by block 502 of flowchart 500. Constants are loaded from registers or a file if stored separately from the program. Typical values will depend on the application. In one embodiment, LDT is set to 21 days, SDT is set to 1 hour, CalAdj is set to 50 ppm, MinConc is set to 425 ppm, and MaxConc is set to 475 ppm. This sets a 50 ppm range centered around a background concentration of 450 ppm. Different applications may require or effectively use different dwell times, background values, and ranges.

At block 502, two timers T1 and T2 are reset. In this examples, the timers count up from 0 to the dwell time values SDT and LDT, respectively, but the timers can alternately be reset to the dwell time values and count down to zero. Finally, a variable MINVAL is initialized to an arbitrarily high value, e.g., a value corresponding to the control SETPOINT of the system when applicable. The program then enters a main loop at block 504, which executes periodically according to an interrupt timer, process schedule for multiple program operating systems, subroutine, larger processing loop when drift correction is integrated into a larger program, etc.

Each time the main loop executes, block 504 retrieves the current sensor value M. In this example, M is the raw value output from the A/D converter (see FIG. 1 for a hardware example). Those skilled in the art will recognize that, alternately, the algorithm can run on processed readings to which the current drift bias correction has already been applied. Further, depending on the hardware design, it is possible that greater A/D outputs represent lower $CO_2$ concentrations—when such is the case, the algorithms are easily adjustable to accommodate this design preference.

At a decision block 506, the processor determines whether reading M is less than the value stored in MINVAL. When the current value is lower, MINVAL is set to M at block 508. The processor then continues in either case to block 510.

At block 510, the processor calculates or retrieves the measured concentration CONC(M) as calculated from the current reading M. The measured concentration is compared to MINCONC. When the measured concentration is less than MINCONC, the sensor has supplied a measurement below the bottom of the background concentration range. In this case, a decision block 514 branches depending on whether T1 is running. If not, T1 is started at block 516 and the routine loops back to block 504 and waits for the next cycle. When the block 510 comparison fails, the sensor is no longer reporting readings below MINCONC, and a block 512 stops and resets T1. Unless T1 has just been started at block 516, both blocks 512 and 514 pass control to a decision block 518.

At block 518, the processor tests timer T1 against the short dwell time SDT. When the timer T1 has reached or exceeded SDT, the criteria have been met for adjusting calibration upward. The processor branches to block 520 and adjusts calibration upward. In this embodiment, an offset constant added during the calculation CONC(M) is adjusted upward by CalAdj (50 ppm). This moves the reported values up 50 ppm, and should place the background measurements within the 50 ppm allowed range (unless the sensor is drifting rapidly). Once a calibration measurement has been made, the routing returns to initialization block 502 and starts over.

Whenever the processor finds at block 518 finds that timer T1 has not equaled or exceeded the short dwell time, control passes to decision block 522. Decision block 522 tests timer T2 against the long dwell time value LDT. When T2 has not equaled or exceeded LDT, the routine loops back to block 504 and waits for the next cycle. Otherwise, control passes to decision block 524.

Anytime block 524 is reached, this indicates that the system has made no calibration adjustments during an entire long dwell time. Decision block 524 computes the concentration corresponding to MINVAL and compares the value to MAXCONC. If MINVAL exceeds MAXCONC, the system has gone an entire long dwell time without ever observing a value in the background concentration range. The processor branches to block 526 and adjusts calibration downward. In this embodiment, the offset constant added during the calculation CONC(M) is adjusted downward by CalAdj (50 ppm). This moves the reported values down 50 ppm, and should place the background measurements within the 50 ppm allowed range (unless the sensor is drifting rapidly). Once a calibration measurement has been made, the routine returns to reset block 502 and begins a new drift correction cycle.

The calibration adjustment need not be a constant value. For instance, if the preset background concentration is 450 ppm, the calibration adjustment can be calculated as:

$$CalAdj = 450 - MINVAL$$

The calibration adjustment as reported by the system can also be phased in over time if desired, to avoid sudden step changes in the reported values. For instance, the periodically reported concentration PPMOUT can be an exponentially filtered version of the measured concentration:

$$PPMOUT = PPMOUT*(1-\alpha) + CONC(M)*\alpha$$

where α is a desired time constant.

Figure 6:
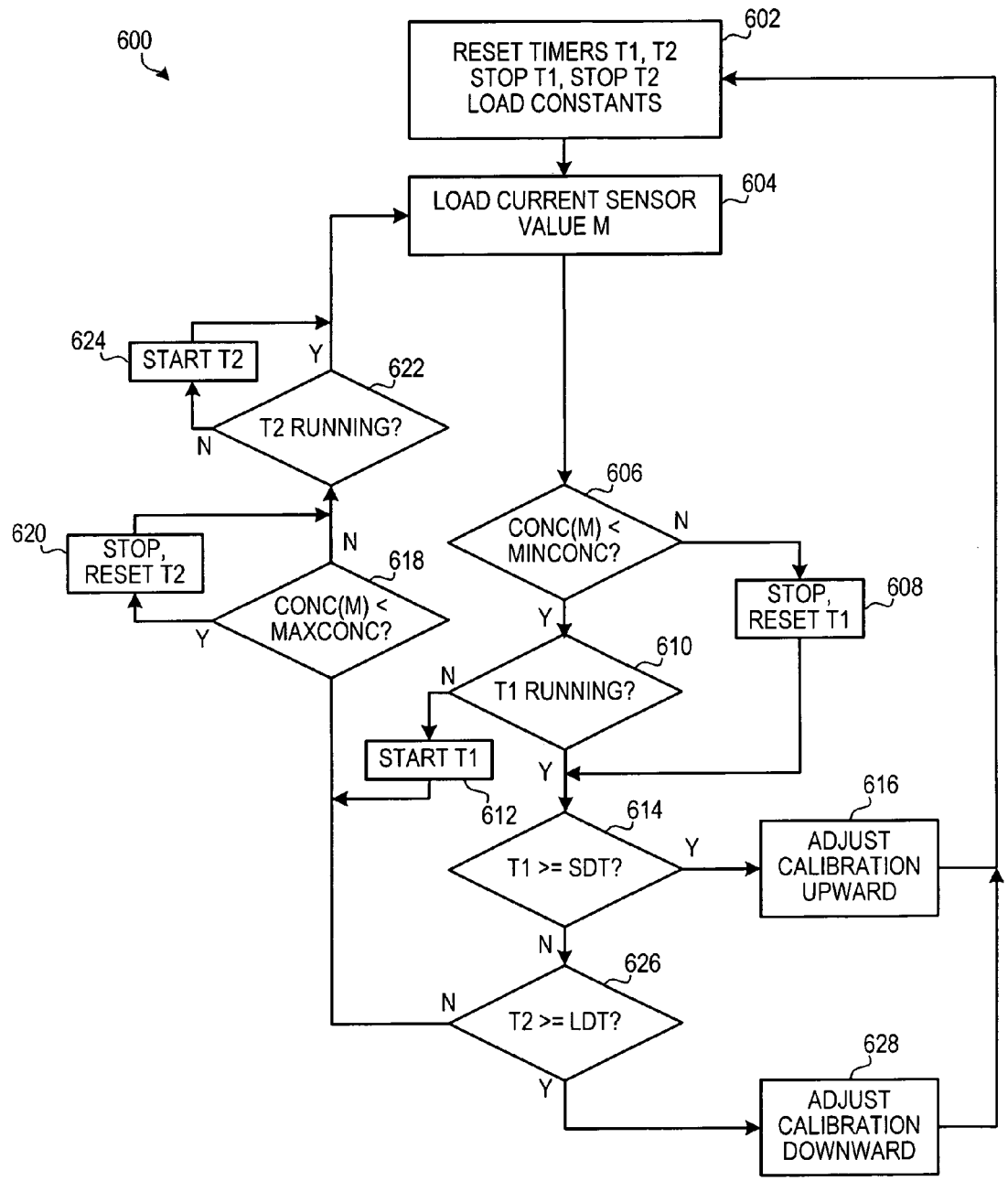

FIG. 6 contains a flowchart 600 for a drift correction method according to another embodiment. This embodiment keeps no historical values at all, and tracks state changes by whether or not timers T1 and T2 are running. A reset block 602, like reset block 502 described above, resets two timers T1 and T2, stops both timers, and loads constants.

Once the drift correction routine 600 is initialized, the processor enters the main loop at block 604. Block 604, like block 504 described above, retrieves the current sensor value M each time the main loop is executed.

At a decision block 606, the processor calculates or retrieves the measured concentration CONC(M) as calculated from the current reading M. The measured concentration is compared to MINCONC. When the measured concentration is less than MINCONC, the sensor has supplied a measurement below the bottom of the background concentration range. In this case, a decision block 610 branches depending on whether T1 is running. If T1 is not running, T1 is started at block 612 and the routine passes control to decision block 618. If T1 is running, the routine passes control to decision block 614. When the block 606 comparison fails, a block 608 stops and resets T1, and then passes control to decision block 614.

At block 614, the processor tests timer T1 against the short dwell time SDT. When the timer T1 has reached or exceeded SDT, the criteria have been met for adjusting calibration upward. The processor branches to block 616 and adjusts calibration upward. In this embodiment, an offset constant added during the calculation CONC(M) is adjusted upward by CalAdj (50 ppm). This moves the reported values up 50 ppm, and should place the background measurements within the 50 ppm allowed range (unless the sensor is drifting rapidly). Once a calibration measurement has been made, the routing returns to initialization block 602 and starts over.

Whenever the processor finds at block 614 that timer T1 has not equaled or exceeded the short dwell time, control passes to decision block 626. Decision block 626 tests timer T2 against the long dwell time value LDT. When T2 has not equaled or exceeded LDT, the routine passes control to decision block 618. Otherwise, control passes to block 628, where the processor adjusts calibration downward. In this embodiment, the offset constant added during the calculation CONC (M) is adjusted downward by CalAdj (50 ppm). This moves the reported values down 50 ppm, and should place the background measurements within the 50 ppm allowed range (unless the sensor is drifting rapidly). Once a calibration measurement has been made, the routine returns to reset block 602 and begins a new drift correction cycle.

Starting and stopping of the long timer T2 is controlled by the flowchart blocks 618, 620, 622, and 624. When the processor executes decision block 618, it compares the current calculated concentration CONC(M) against MAXCONC. If the concentration is less than MAXCONC, block 620 stops and resets T2 since the result of the test indicates that the sensor is still measuring values in the allowable background concentration range. Decision block 622 next causes the processor to test whether T2 is running, and when T2 is not running, block 624 starts T2. The process then loops back to block 604 and awaits the next execution cycle.

One difference between the FIG. 5 and FIG. 6 methods is that, as long as no upward calibration is attempted, flowchart 500 continues to count T2 towards LDT, even if a reading below MAXCONC has been achieved since the last time T2 has been reset. Only when T2 reaches LDT is a test against MAXCONC made. This means that in the worst case, almost 2 LDT time periods may pass before an upwards drift is corrected. Flowchart 600, on the other hand, resets and restarts T2 each time a concentration below MAXCONC is seen. Thus flowchart 600 will make a needed upwards drift correction after one LDT period from the last time a reading in range was seen. Whether the flowchart 500 or the flowchart 600 behavior is preferred will depend on the application and possibly the sensor characteristics.

Figure 1:
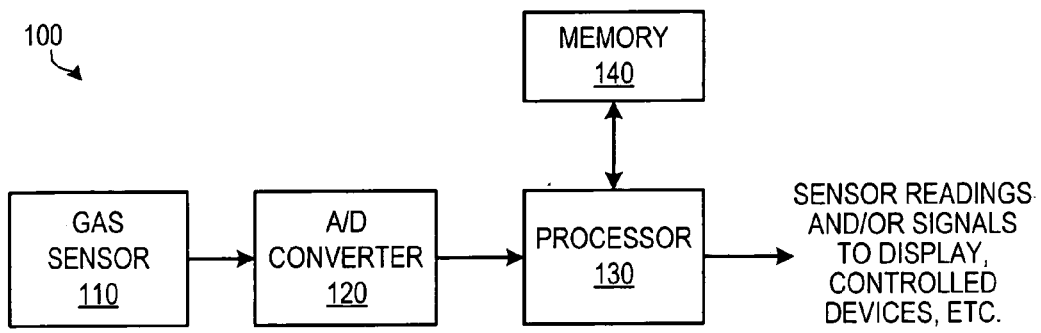
FIG. 1 contains a block diagram for a prior art environmental gas sensor.
Figure 4:
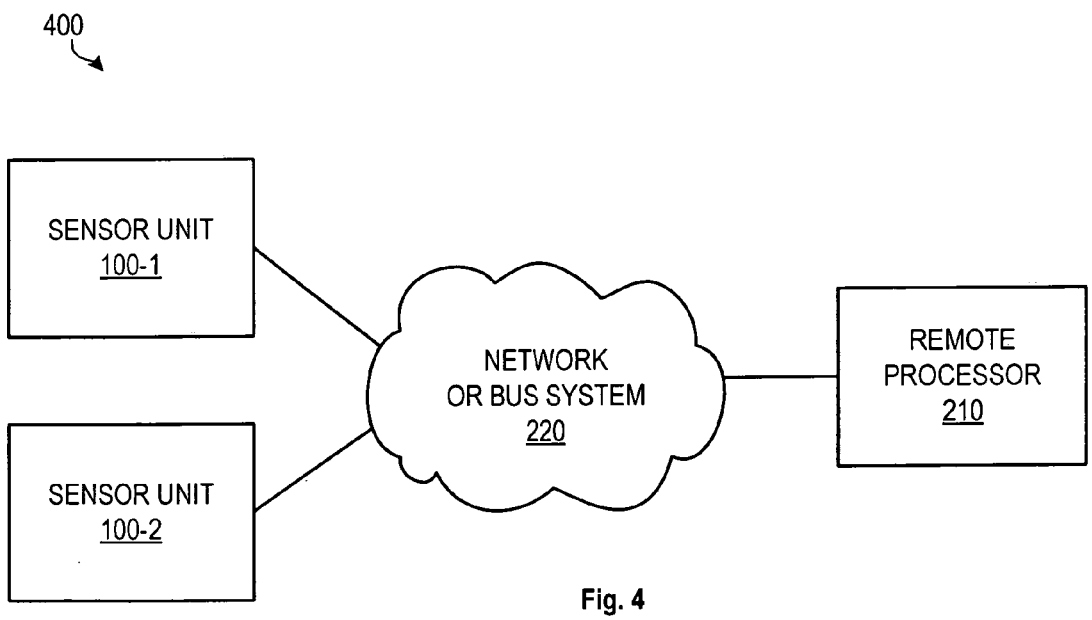
FIG. 4 contains a block diagram for an alternate environmental gas sensor configuration applicable to an embodiment.
Figure 2:
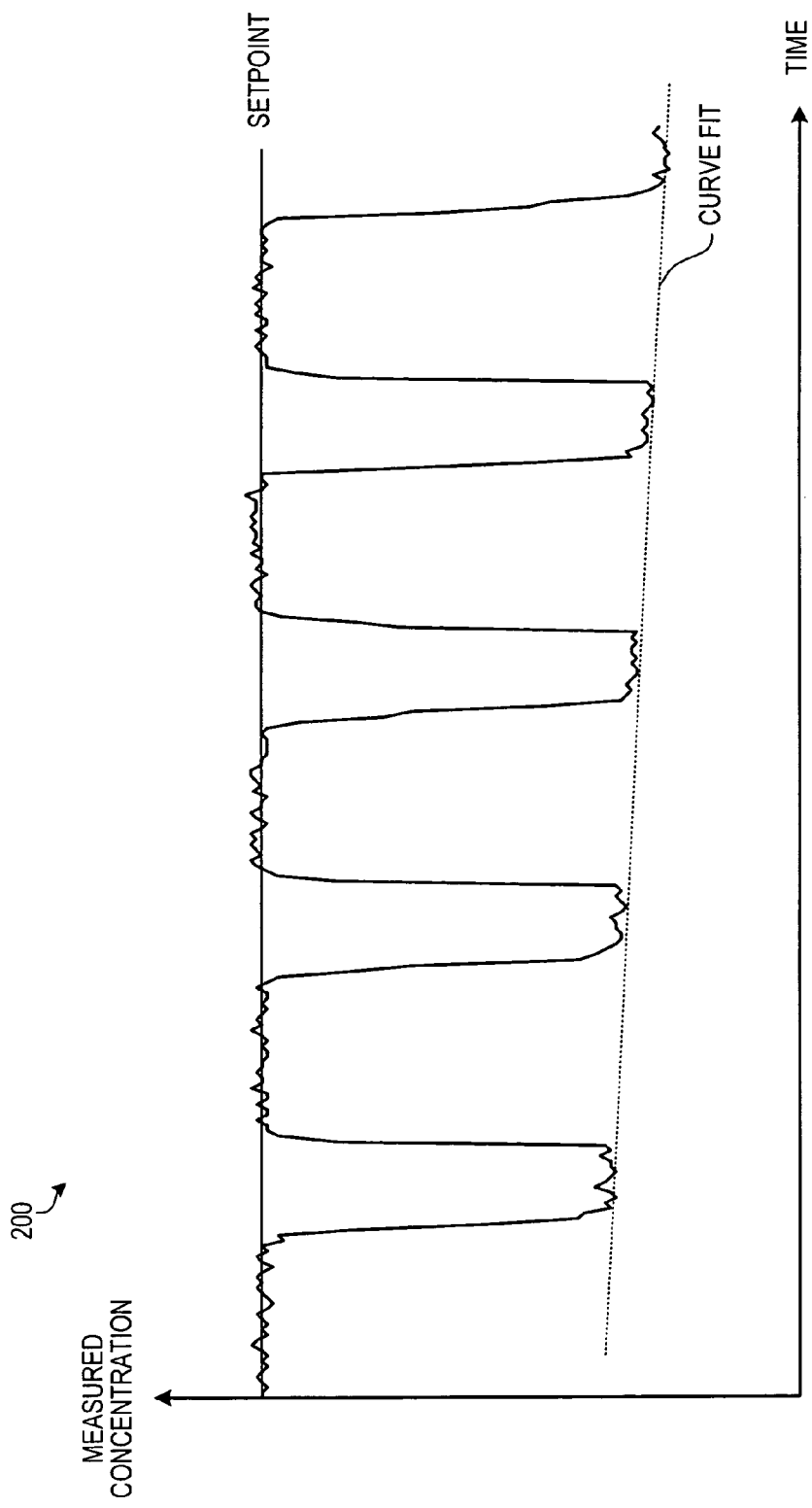
FIGS. 2 and 3 contain graphs of sensor readings over time, showing respectively downward and upward sensor drift, and a prior art method of compensating for such drift.
Figure 3:
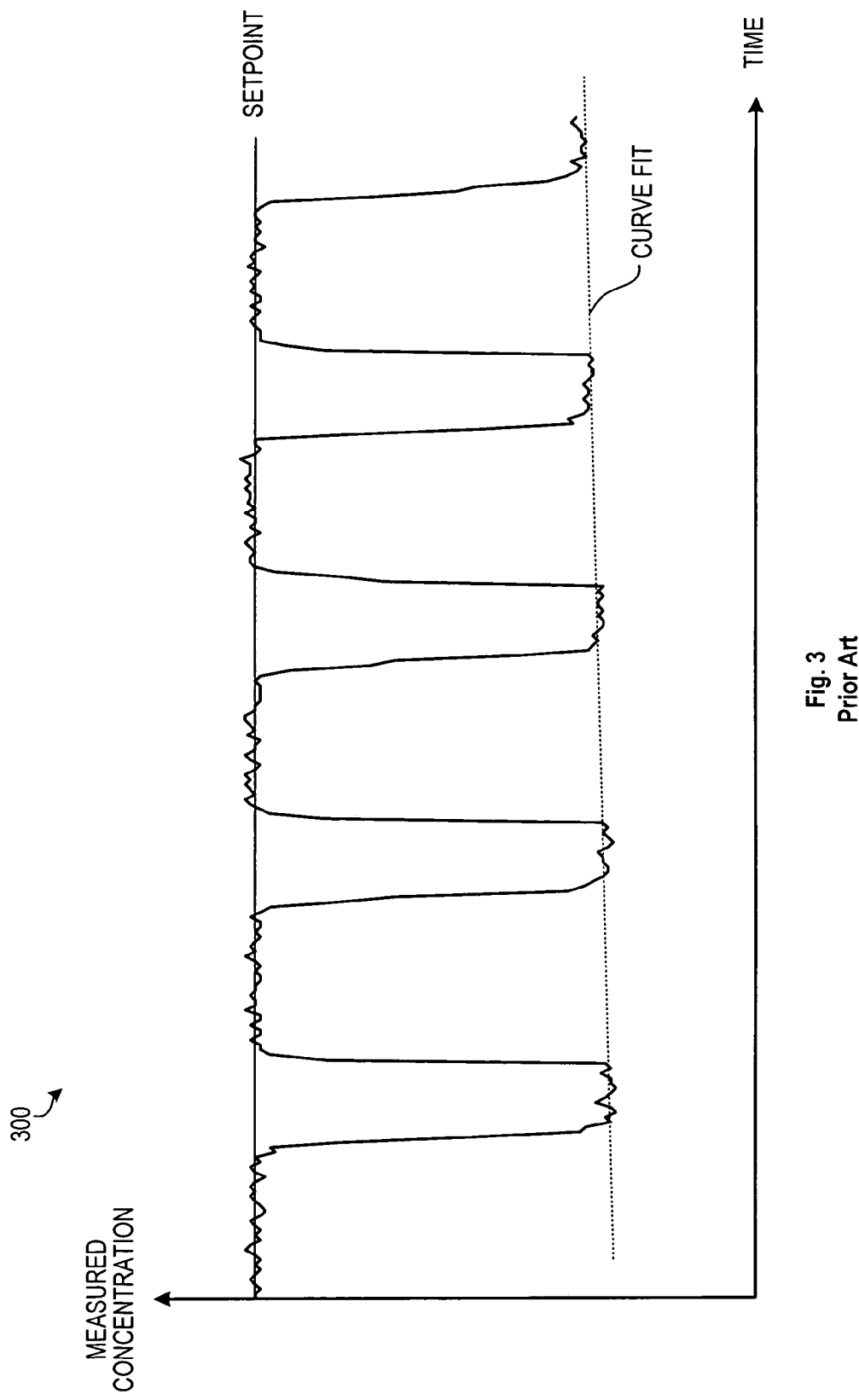

Drift compensation embodiments can be implemented on a processor/memory system that is packaged with the gas sensor, such as the system 100 shown in block diagram form in FIG. 1. Alternately, a remote system that receives concentration readings from one or more sensor units can correct drift on the remote readings. FIG. 4 shows such a system as a block diagram 400. Two sensor units 100-1 and 100-2 connect to a remote processor 210 through a network or bus system 220. Each sensor unit reports non-drift-corrected concentration readings to remote processor 210. Remote processor 210 runs separate timers, e.g., according to method 500 or 600, for each sensor unit, to perform drift correction. The sensor units and remote processor can be in a common housing, e.g., with pluggable sensor modules, or placed in sensing locations that are hard to access, distant from a control system operated by the remote processor, or in an environment detrimental to such a control system.

Figure 7:
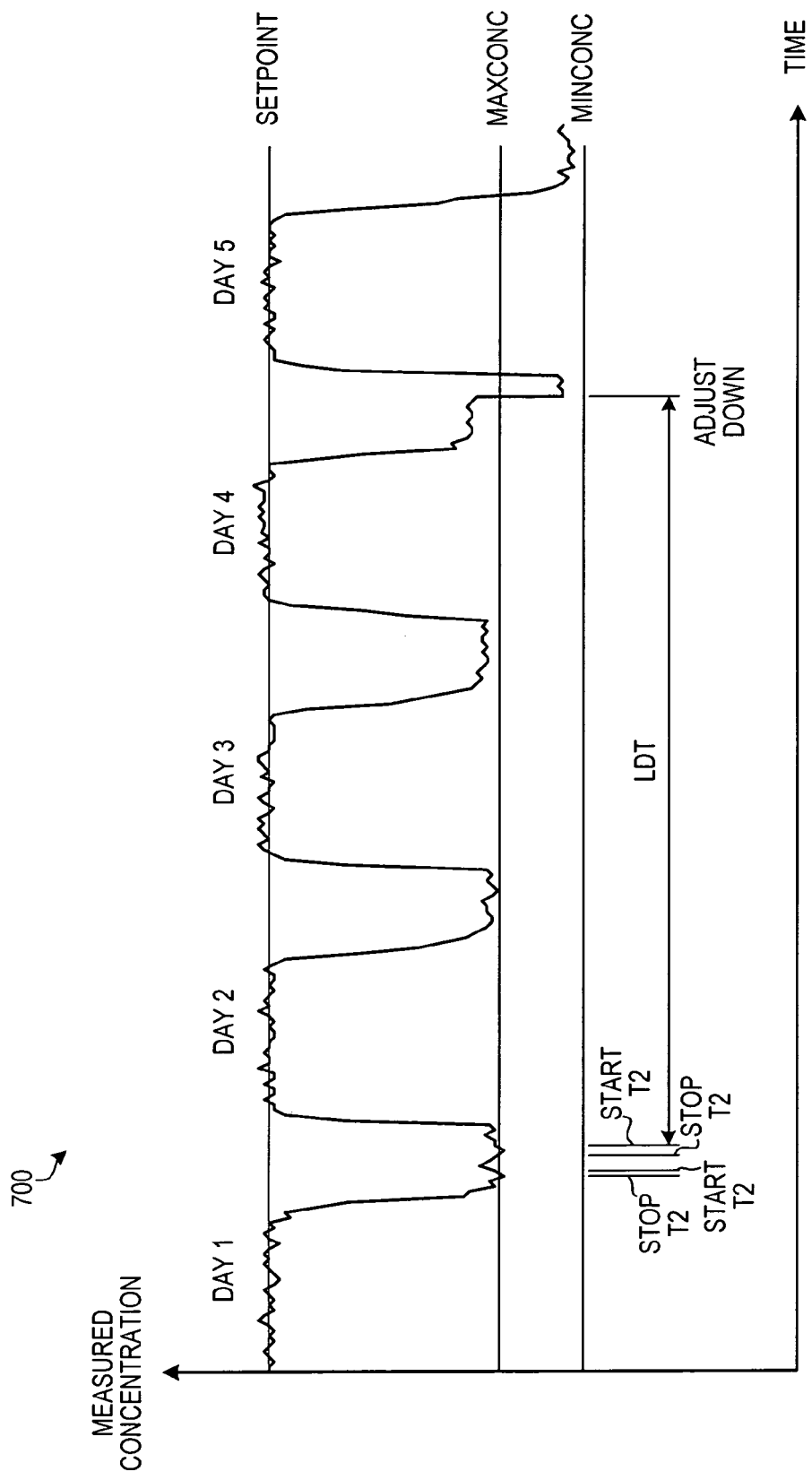
FIGS. 7, 8, and 9 contain graphs of sensor readings over time, showing examples of drift corrections according to an embodiment.

FIG. 7 contains a plot 700 of measured concentration vs. time, for a sensor utilizing drift correction according to method 600. A MINCONC to MAXCONC background concentration range and a SETPOINT concentration are shown. In plot 700, the concentration varies in a daily cycle between setpoint-control led occupied times and background level unoccupied times.

Timer T2 is running at the start of the plot, as the concentration is high. Near the end of Day 1, the concentration dips below MAXCONC twice, each time stopping timer T2 (by definition, when the sensor operates in the background concentration range no drift correction is needed). As the concentration rises above MAXCONC, however, this causes T2 to begin running again.

Due to a slow upward drift in the sensor output, during the unoccupied times of days 2, 3, and 4, the background level never drops below MAXCONC. Thus T2 continues to run, and reaches the LDT dwell time (72 hours in this example) during the night of day 4. This triggers a downward calibration adjustment of (MAXCONC−MINCONC) in this example, dropping the background readings well into the desired range. On day 5, the background level operates in the desired range.

Figure 8:
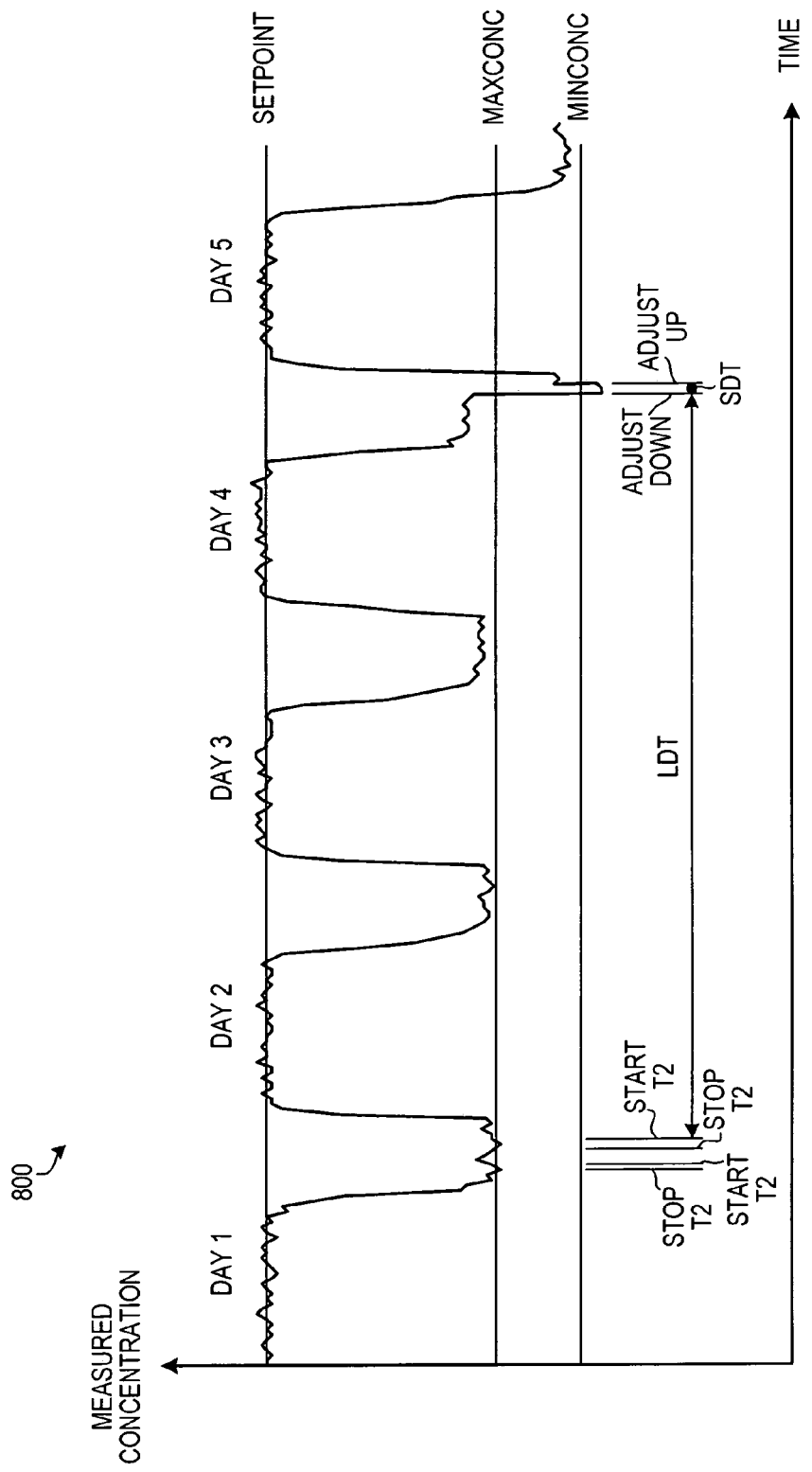

FIG. 8 contains a plot 800 for the same raw readings, but with a different correction technique. At the end of day 4, when T2 reaches LDT, the downward calibration adjustment is made as 2*(MAXCONC−MINCONC). Because downward adjustments can occur less frequently than upward adjustments to provide safety when the monitored environment unexpectedly goes many days without being unoccupied, there is the potential for more drift in the upward direction. A larger adjustment compensates for a potentially larger drift.

In plot 800 the upward drift was not large, and therefore the downward adjustment actually placed the background level below MINCONC. Assuming that the correction occurred during a background reading interval, SDT minutes later an upwards adjustment would occur to place the reported background reading back in range. The upwards adjustments are smaller than the downwards adjustments, as they can occur much more frequently.

Figure 9:
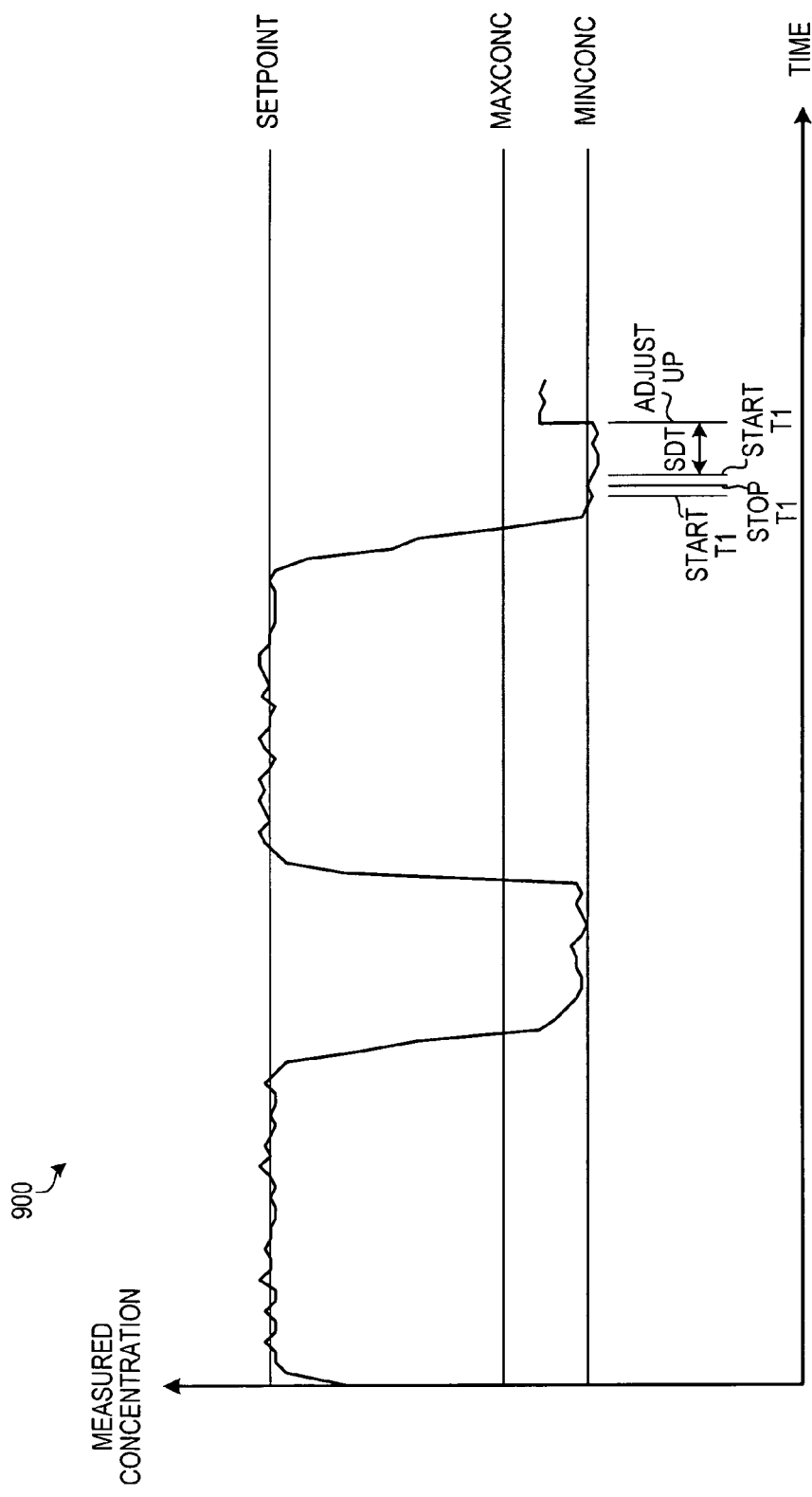

FIG. 9 contains a plot 900 showing more detail of an upwards drift correction, for a sensor utilizing drift correction according to method 600. A MINCONC to MAXCONC background concentration range and a SETPOINT concentration are shown. In plot 700, the concentration varies in a daily cycle between setpoint-controlled occupied times and background level unoccupied times.

During the first non-occupied period shown, the measured concentration remains in the preset background concentration range. During the second non-occupied period shown, the measured concentration drifts below MINCONC, bumps back up to MINCONC, and then descends below MINCONC again. On both occurrences of a drift below MINCONC, timer T1 starts. The processor stops T1 the first time as the dwell below MINCONC is shorter than the short dwell time SDT. On the second drift below MINCONC, timer T1 starts and runs for the full dwell time SDT. This triggers an upward adjustment, e.g., by a value (MAXCONC−MINCONC)/2. The short dwell timer avoids drift adjustments due to a noisy reading or a brief application of null gas (calibration gas without the measured constituent present).

The length of the long dwell timer is set to avoid inadvertent resets should the expected occupied-unoccupied pattern be upset for an extended time period. For instance, the suggested three-week time frame should avoid most situations where the system would otherwise be fooled because the background level is never reached due to the monitored location being occupied continuously for several weeks.

Another way to allow more rapid adjustment while avoiding inadvertent resets is to count the number of significant dips since T2 was started, where a dip is defined, e.g., as an excursion halfway from the SETPOINT to MAXCONC that lasts for at least a time period T1. When N such excursions are observed, a downwards drift correction may be allowed even when LDT has not yet expired.

Although timers are suggested, other equivalent methods could be used to discern drift patterns, such as a credit/debit system. One such system keeps a MAXCREDIT counter (e.g., preset to 20, capped at 30) and a MINCREDIT counter (e.g., set to 2, capped at 3). Each day, MAXCREDIT is decremented if the measured value (or a filtered version thereof to ignore noise) never drops below MAXCONC, and incremented otherwise. Should MAXCREDIT reach 0, a downward adjustment is triggered and the drift correction system resets. Each day, MINCREDIT is decremented in the measured value or filtered version thereof never drops below MINCONC, and incremented otherwise. Should MINCREDIT reach 0, an upward adjustment is triggered and the drift correction system resets.

Those skilled in the art will appreciate that the embodiments and/or various features of the embodiments can be combined in ways other than those described. The background concentration range can be asymmetric about the expected background concentration value. Many possibilities exist for the type of adjustment made—e.g., the calibration adjustment can move the present minimum, or the minimum observed during the current time period, exactly to the expected background concentration value. Other hybrid implementations, such as a timer-based adjustment for upward adjustments and credit-based adjustment for downward adjustments, are possible. The sensor measurements can be stored in a history log, and evaluated after the fact by the processor to declare an adjustment, rather than evaluating the measurements in real time. Although NDIR CO2 sensors provide illustrative applications, embodiments are adaptable to other environmental gas sensors.

Although the specification may refer to "an", "one", "another", or "some" embodiment(s) in several locations, this does not necessarily mean that each such reference is to the same embodiment(s), or that the feature only applies to a single embodiment.

What is claimed is:

1. A method of compensating for sensor drift in an environmental gas sensor, the method comprising:
    maintaining in a computer memory a representation of a background gas concentration range for a gas sensor, the background gas concentration range existing between a minimum sensor reading low value and a minimum sensor reading high value, the minimum sensor reading low value corresponding to a first gas concentration value and the minimum sensor reading high value corresponding to a second gas concentration value, higher than the first gas concentration value;
    maintaining in the computer memory criteria for declaring patterns in background gas concentration readings based on the background gas concentration range;
    accepting recurring gas concentration readings from the gas sensor;
    analyzing the recurring gas concentration readings against the maintained criteria with a processor coupled to the computer memory, wherein analyzing comprises determining whether the concentration readings indicate the presence of a pattern of background gas concentration readings either lower than the minimum sensor low value or greater than the minimum sensor reading high value;
    when analysis of the recurring gas concentration readings indicates the presence of a pattern of background gas concentration readings lower than the minimum sensor reading low value, adjusting an indicated gas concentration upwards; and
    when analysis of the recurring gas concentration readings indicate the presence of a pattern of background gas concentration readings greater than the minimum sensor reading high value, adjusting the indicated gas concentration downwards.

2. The method of claim 1, wherein the criteria for declaring patterns in the background gas concentration readings comprise criteria for adjusting the indicated gas concentration upwards and downwards, the criteria for adjusting the indicated gas concentration upwards differing from the criteria for adjusting the indicated gas concentration downwards.

3. The method of claim 2, wherein the criteria for adjusting the indicated gas concentration upwards comprise a first dwell time during which the recurring gas concentration readings correspond to a measured gas concentration below the first gas concentration value.

4. The method of claim 3, wherein the criteria for adjusting the indicated gas concentration downwards comprise a second dwell time during which the recurring gas concentration readings correspond to a measured gas concentration above the second gas concentration value.

5. The method of claim 4, wherein the first dwell time is set to a value less than three hours and the second dwell time is set to a value of at least three days.

6. The method of claim 4, wherein the criteria for adjusting the indicated gas concentration downwards further comprises an excursion count.

7. The method of claim 6, wherein analyzing the recurring gas concentration readings with a processor comprises running a timer while the recurring gas concentration readings remain higher than the second gas concentration value, and keeping an excursion count tally indicating the number of times during the current period timed by the timer that the indicated gas concentration crosses from above to below a third gas concentration value, higher than the second gas concentration value, and comparing the excursion count tally to the excursion count.

8. The method of claim 7, wherein analysis of the recurring gas concentration readings indicate the presence of a pattern of background gas concentration readings greater than the minimum sensor reading high value either when the timer reaches or exceeds a first value and the excursion count tally reaches or exceeds the excursion count, or when the timer reaches or exceeds the second dwell time.

9. The method of claim 4, wherein analyzing the recurring gas concentration readings with a processor comprises running a timer while the recurring gas concentration readings remain higher than the second gas concentration value, and wherein analysis of the recurring gas concentration readings indicate the presence of a pattern of background gas concentration readings greater than the minimum sensor reading high value when the timer reaches or exceeds the second dwell time.

10. The method of claim 3, wherein analyzing the recurring gas concentration readings with a processor comprises running a timer while the recurring gas concentration readings remain lower than the first gas concentration value, and wherein analysis of the recurring gas concentration readings indicate the presence of a pattern of background gas concentration readings lower than the minimum sensor reading low value when the timer reaches or exceeds the first dwell time.

11. The method of claim 1, wherein adjusting the gas concentration comprises adjusting a drift correction parameter by a calibration adjustment value that is independent of drift rate.

12. The method of claim 11, wherein the calibration adjustment value is a constant related to the size of the background concentration range.

13. The method of claim 11, wherein the defined calibration adjustment value is greater for downwards adjustments than for upwards adjustments.

14. The method of claim 11, wherein the calibration adjustment value is related to the difference between a preset gas concentration value in the background gas concentration range and a minimum gas concentration reading during a time period indicative of the presence of a pattern of background gas concentration readings.

15. An apparatus comprising a non-transitory computer readable medium containing executable code that, when executed by one or more processors, causes the one or more processors to perform the method of claim 1.

16. A data processing system comprising:
a processor;
an input port for receiving recurring gas concentration readings from a gas sensor;
a memory system storing executable code for the processor, the processor executing the executable code to perform drift compensation on the recurring gas concentration readings by analyzing the recurring gas concentration readings, wherein analyzing comprises determining whether the concentration readings indicate the presence of a pattern of background gas concentration readings either lower than a minimum sensor low value or greater than a minimum sensor reading high value, and when analysis of the recurring gas concentration readings indicates the presence of a pattern of background gas concentration readings lower than the minimum sensor reading low value, adjusting an indicated gas concentration upwards, and when analysis of the recurring gas concentration readings indicate the presence of a pattern of background gas concentration readings greater than the minimum sensor reading high value, adjusting the indicated gas concentration downwards.

17. The data processing system of claim 16, wherein the data processing system and the gas sensor exist in a common assembly.

18. The data processing system of claim 17, wherein the data processing system couples remotely to the gas sensor.

19. The data processing system of claim 16, wherein the processor performs drift correction on the recurring gas concentration readings without reference to any of the recurring gas concentration readings except a current one of the gas concentration readings, by maintaining state variables representative of time spent outside of the range between the minimum sensor reading low and high values.

20. The data processing system of claim 16, wherein upward drift correction requires less than one day of recurring gas concentration readings, and downward drift correction requires multiples days of recurring gas concentration readings.

* * * * *